US009759652B2

(12) United States Patent  
Yu

(10) Patent No.: US 9,759,652 B2  
(45) Date of Patent: Sep. 12, 2017

(54) QUANTUM DOT LIGHT EMITTING DIODES FOR MULTIPLEX GAS SENSING

(71) Applicant: Weiyong Yu, Shreveport, LA (US)

(72) Inventor: Weiyong Yu, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/055,956

(22) Filed: Feb. 29, 2016

(65) Prior Publication Data

US 2016/0252458 A1  Sep. 1, 2016

Related U.S. Application Data

(60) Provisional application No. 62/126,495, filed on Feb. 28, 2015.

(51) Int. Cl.
| | |
|---|---|
| *G01N 21/64* | (2006.01) |
| *G01N 21/31* | (2006.01) |
| *G01N 21/03* | (2006.01) |
| *G01N 21/25* | (2006.01) |
| *B82Y 15/00* | (2011.01) |

(52) U.S. Cl.  
CPC ........... *G01N 21/31* (2013.01); *G01N 21/031* (2013.01); *G01N 21/255* (2013.01); *B82Y 15/00* (2013.01); *G01N 2201/062* (2013.01); *Y10S 977/954* (2013.01)

(58) Field of Classification Search  
CPC ..... G01N 2201/062; G01N 2021/7786; G01N 21/6489; G01N 21/31; B82Y 15/00; B82Y 20/00; Y10S 977/954

USPC ........................................................ 250/459.1  
See application file for complete search history.

(56) References Cited

U.S. PATENT DOCUMENTS

| | | | | |
|---|---|---|---|---|
| 5,488,227 A * | 1/1996 | Sweet | ................... | G01N 21/031 250/343 |
| 6,016,203 A * | 1/2000 | Martin | ...................... | G01J 3/18 356/432 |
| 6,194,735 B1 * | 2/2001 | Martin | ................... | G01N 21/031 250/222.2 |
| 7,616,316 B1 * | 11/2009 | Silver | .................... | G01N 21/39 356/409 |
| 7,922,355 B1 * | 4/2011 | Morejon | ................... | F21K 9/54 362/247 |
| 2006/0071218 A1 * | 4/2006 | Takeda | .................. | B82Y 10/00 257/79 |
| 2007/0024173 A1 * | 2/2007 | Braune | ................. | H01L 33/502 313/485 |
| 2007/0279633 A1 * | 12/2007 | Yi | ........................ | G01N 21/031 356/432 |
| 2008/0303985 A1 * | 12/2008 | Hayashi | ............. | C09K 19/2007 349/88 |

(Continued)

FOREIGN PATENT DOCUMENTS

CN  104091864 A  * 10/2014

*Primary Examiner* — Kiho Kim  
(74) *Attorney, Agent, or Firm* — Davis & Bujold, P.L.L.C.; Charles Holoubek

(57) ABSTRACT

A gas detection device comprising a light emitting source including a first plurality of quantum dots of substantially discrete size and made of a semiconductor material a gas cell to contain the gas to be detected and a light detector.

20 Claims, 23 Drawing Sheets

(56) References Cited

U.S. PATENT DOCUMENTS

| | | | |
|---|---|---|---|
| 2010/0110437 A1* | 5/2010 | Furtaw | G01K 13/02 356/437 |
| 2010/0264333 A1* | 10/2010 | Offermans | B82Y 15/00 250/459.1 |
| 2011/0188039 A1* | 8/2011 | Aoyama | G01N 21/53 356/338 |
| 2013/0048922 A1* | 2/2013 | Zhou | C01B 19/007 252/519.3 |
| 2014/0339437 A1* | 11/2014 | Aziz | H01L 51/502 250/458.1 |
| 2016/0054220 A1* | 2/2016 | Nishijima | G01N 21/3504 356/409 |

* cited by examiner

| Gas sample | Sample C1 | Sample C2 | Sample C3 | Sample C4 | Sample C5 |
|---|---|---|---|---|---|
| $C_2H_2$ (ppm) | 100 | 250 | 400 | 550 | 700 |
| $CH_4$ (ppm) | 1000 | 3000 | 5000 | 7000 | 9000 |
| $NH_3$ (ppm) | 100 | 250 | 400 | 550 | 700 |

QUANTUM DOT LIGHT EMITTING DIODES FOR MULTIPLEX GAS SENSING

CROSS REFERENCE TO RELATED APPLICATIONS/PRIORITY

The present invention claims priority to U.S. Provisional Patent Application No. 62/126,495, filed on Feb. 28, 2015, which is incorporated by reference into the present disclosure as if fully restated herein. To the extent that there is any conflict between the incorporated material and the present disclosure, the present disclosure will control.

FIELD OF THE INVENTION

The present invention relates to the field of quantum dot light emitting diodes for gas sensing, detection, and identification.

BACKGROUND OF THE INVENTION

The detection and quantification of gas, especially the flammable and poisonous gases in air are extremely important due to their great demands in areas such as environmental monitoring, coal mine safety, industrial production, and automobile exhaust monitoring, etc. A number of methods have been used to detect gas species including spectroscopy, electrochemistry, and photoacoustics, each having various disadvantages. Multiple gases often co-exist in complicated environments, further complicating design successful of detection devices. For example, the gas in coal mines may compose methane ($CH_4$), ammonia ($NH_3$), carbon monoxide (CO), sulfur dioxide ($SO_2$), hydrogen sulfide ($H_2S$), etc. $CH_4$ is unavoidable to be released during the coal mining and it outbursts in both underground and surface mines, but must be tracked and monitored. When $CH_4$ reaches a concentration of 5-15% in air in a closed environment, $CH_4$ becomes dangerously explosive. Similarly, $C_2H_2$ and $NH_3$ are released during industrial production and they are extremely explosive gases when their concentrations reach 2.5%-80% and 16-25%, respectively. Therefore, multiplex gas detection is quite necessary, and usually several wavelengths are required for the simultaneous multiplex gas detection using spectroscopy method. Traditional instrument's light sources usually generate single wavelength light, and their physical site is bulky, their optical stability and specificity are low. Additionally, simultaneous detection and measurement of multiple gases is difficult.

SUMMARY OF THE INVENTION

Wherefore, it is an object of the present invention to overcome the above mentioned shortcomings and drawbacks associated with the prior art.

The inventor has observed that semiconductor quantum dots (QDs) usually possess high photoluminescence (PL) quantum yield (QY) with size dependent tunable wavelength emission that make them promising, light emitting diodes (LEDs) as light sources, which can be used for the optical detection and measurement of gases.

The present invention relates to making multi-wavelength light emitting diodes (LEDs) without mutual-absorption using QDs. The LEDs emit multiple emission wavelengths for detecting multiple gases simultaneously through direct absorption spectroscopy.

The present invention relates to a gas detection device and method including a light emitting source including a first plurality of quantum dots of substantially discrete size and made of one or more semiconductor materials, a gas cell to contain the gas to be detected, and, light detector.

Further optional embodiments include a convex mirror arrangement to increase a light path through the gas cell to multiple times a length of the gas cell.

Further optional embodiments include a first layer of quantum dots including the first plurality of quantum dots, a second layer of quantum dots includes a second plurality of quantum dots, and the first plurality of quantum dots being one of substantially different size, substantially different composition, and both substantially different size and substantially different composition compared to second plurality of quantum dots.

Further optional embodiments include a third layer of quantum dots including a third plurality of quantum dots, and the third plurality of quantum dots being one of substantially different size, substantially different composition, and both substantially different size and substantially different composition compared to each of the first and the second plurality of quantum dots.

Further optional embodiments include the first and/or second and/or third plurality of quantum dots including at least one of Pb, Se, S, Te, Zn, Cd, Cu, In, and a combination thereof.

Further optional embodiments include first and/or second and/or third plurality of quantum dots including at least one of PbSe, PbS, PbTe, ZnS, ZnSe, CdSe, CdTe, CdS, $CuInS_2$, and InP.

Further, optional embodiments include first and/or second and/or third plurality of quantum dots are between 4 nm and 7 nm in size.

Further optional embodiments include the first and/or second and/or third plurality of quantum dots exhibit photoluminescence with a wavelength emission in at least one of Infra-red, Near Infra-Red, visible, and ultraviolet wavelengths of light.

Further optional embodiments include the light emitting source including a multi-wavelength light emitting diode.

Further optional embodiments include the multi-wavelength light emitting diode not exhibiting mutual-absorption.

Further optional embodiments include the first and/or second and/or third plurality of quantum dot includes a material with a quantum yield of at least 85%.

The present invention further relates to a device for and method of detecting one or more gasses using a light, emitting source having at least a first plurality of semiconductor quantum dots of substantially discrete size, a gas cell to contain the gas to be detected and a light detector. The method comprises the steps of energizing the light emitting source, emitting first light waves from the first plurality of quantum dots, and passing the first light waves through a gas sample in the gas cell and into a light detector.

Further optional embodiments include the light emitting source including a second plurality of semiconductor quantum dots of substantially discrete size and further comprising the step of emitting second light waves from the second plurality of quantum dots and passing the second light waves through the gas sample in the gas cell and into a light detector.

Further optional embodiments include the light emitting source including a third plurality of semiconductor quantum dots of substantially discrete size and further comprising the step of emitting third light waves from the third plurality of quantum dots, passing the third light waves through the gas sample in the gas cell and into a light detector, and the first, second, and third light waves being emitted at substantially a same first time and the first, second, and third light waves are detected at substantially a same second time.

Further optional embodiments include the gas sample containing one of a single gas, more than one gas, and at least three gasses.

Further optional embodiments include one of detecting at least one gas and detecting two or more gases.

Further optional embodiments include reflecting the first light waves off of mirrors and passing the first light waves through the gas sample more than once before passing the first light waves into a light detector.

Further optional embodiments include first layer being adjacent to one of a blue or ultraviolet light emitting diode chip; the first plurality of quantum dots having a first wavelength photoluminescence emission; the second layer being adjacent to the first layer and the second plurality of quantum dots having a second wavelength photoluminescence emission that is shorter than the first wavelength, and the third layer being adjacent to the second layer and spaced from the first layer by the second layer, and the third plurality of quantum dots having a third wavelength photoluminescence emission that is shorter than the first and the second wavelength.

The present invention additionally relates to a gas detection device and method comprising a non-mutually absorption multi-wavelength light emitting diode; the light emitting source including a first plurality of quantum dots of substantially discrete size and made of a semiconductor material, a second plurality of quantum dots of substantially discrete size and made of a semiconductor material, and a third plurality of quantum dots of substantially discrete size and made of a semiconductor material; the first plurality of quantum dots are one of substantially different size, substantially different composition, and both substantially different size and substantially different composition compared to second and the third plurality of quantum dots; the second plurality of quantum dots are one of substantially different size, substantially different composition, and both substantially different size and substantially different composition compared to third plurality of quantum dots; the light emitting source including at least three layers, the first layer including the first plurality of quantum dots and not the second or third pluralities of quantum dots, the second layer including the second plurality of quantum dots and not the first or third pluralities of quantum dots, and the third layer including the third plurality of quantum dots and not the first or section pluralities of quantum dots; a gas cell to contain the gas to be detected; the cell including a convex mirror arrangement to increase a light path through the gas cell to multiple times a length of the gas cell; a light detector; one of the first, the second, and the third pluralities of quantum dots includes at least one of PbSe, PbS, PbTe, ZnS, ZnSe, CdSe, CdTe, CdS, CuInS$_2$, and InP; the first, the second, and the third pluralities of quantum dots are between 4 nm and 7 nm in size; and the first, the second, and the third pluralities of quantum dots each exhibit photoluminescence with a wavelength emission in at least one of Infra-red, Near Infra-Red, visible, and ultraviolet wavelengths of light.

Various objects, features, aspects, and advantages of the present invention will become more apparent from the following detailed description of preferred embodiments of the invention, along with the accompanying drawings in which like numerals represent like components.

BRIEF DESCRIPTION OF THE DRAWING

The accompanying drawings, which are incorporated in and constitute a part of the specification, illustrate various embodiments of the invention and together with the general description of the invention given above and the detailed description of the drawings given below, serve to explain the principles of the invention. The invention will now be described, by way of example, with reference to the accompanying drawings in which.

DETAILED DESCRIPTION OF THE INVENTION

Figure 1:
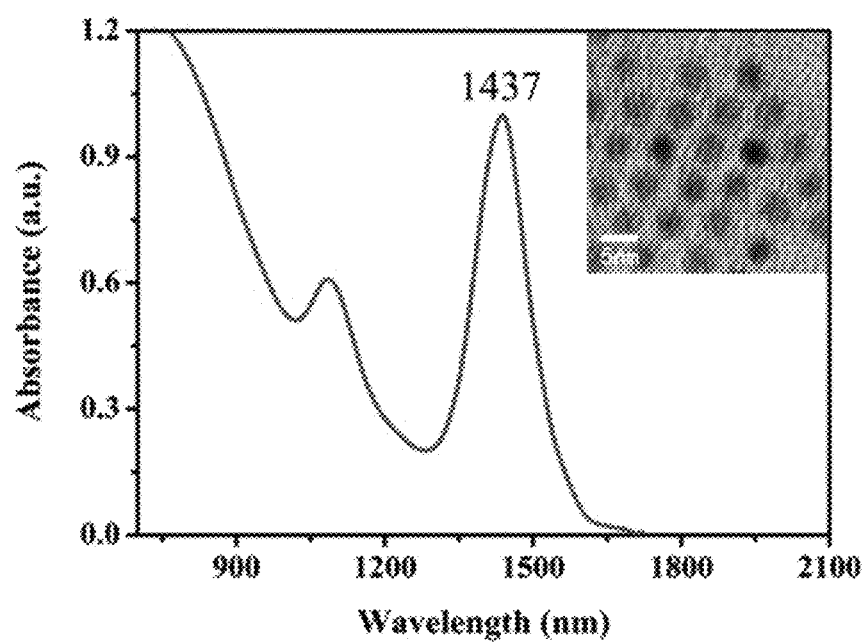
FIG. 1 is a normalized absorption spectrum and Transmission Electron Microscopy (TEM) image of 4.6 nm PbSe QDs.

The present invention will be understood by reference to the following detailed description, which should be read in conjunction with the appended drawings. It is to be appreciated that the following detailed description of various embodiments is by way of example only and is not meant to limit, in any way, the scope of the present invention.

This patent application describes a design and fabrication of non-mutual-absorption QD-LEDs with multiple emitting wavelengths using QDs and an excitation light source. The excitation light source having a light wavelength within the QD's absorption range, for example, a blue or ultraviolet GaN LED. The disclosed method and apparatus shows good selectivity of multiplex gas simultaneous concentration measurement indicating that the disclosed QD-LED light sources have great potential in many fields on account of their low-cost, small size, high efficiency, and multiplex detection. Near infrared (NIR) QD-LEDs are described in detail because many simple but flammable gases have strong absorption in NIR range. The NIR QD-LED design is also good for visible QD-LEDs and the gas detection with visible range absorption.

PbSe bulk material has a small band gap of 0.28 eV at room temperature and a very large exciton Bohr radius of 46 nm. As a result, PbSe QDs show very strong quantum confinement and high quantum yield (QY). The PbSe QDs' QY can easily reach 85% or higher in NIR region. PbSe QDs' band edge absorption peaks span over a wide infrared wavelength region of 1-4 µm. An LED emitting 3 NIR wavelengths using PbSe QDs is described as an example. The as-fabricated NIR LEDs are then applied to detect three gases ($NH_3$, $CH_4$ and $C_2H_2$) at the same time based on direct absorption spectroscopy. These three gasses are just an example of the detection abilities of the gas detector using QD-LEDs.

The PbSe QDs employed in the present study were synthesized according to the method reported by Yu et al. (Yu, W. W.; Falkner, J. C.; Shih, B. S.; and Colvin, V. L.) Preparation and characterization of monodisperse PbSe semiconductor nanocrystals in a noncoordinating solvent. *Chem. Mater.* 2004, 16, 3318-3322.). The method is described in the article is incorporated herein by reference. Briefly, a mixture of 0.892 g PbO, 2.26 g oleic acid (OA), and 12.848 g 1-octadecene (ODE) were loaded into a 100 mL three-neck flask. After 10 minutes nitrogen flow to remove the oxygen, the three-neck flask was heated to 170° C. After PbO powder completely disappeared and the solution became colorless, 6.9 mL Se-trioctylphosphine solution (containing 0.637 g Se powder) was quickly injected into the vigorously stirred solution. The temperature of the reaction mixture was then maintained at 143° C. for QD growth. At a certain reaction time, 30 mL, of toluene was injected into the three-neck flask and then the flask was submerged in a room-temperature water bath to completely quench the reaction. A series of purification operation procedures were carried out to remove excess reaction precursors and ODE before utilization. QDs were purified by phase extraction twice with methanol and precipitation once with acetone. The final products were dispersed in chloroform for LED fabrication and stored in an argon filled container.

UV-Vis absorption spectra were recorded using a Shimadzu IN-3600 UV-visible spectrophotometer. The photoluminescence properties of PbSe QDs in chloroform solutions and the spectra properties of LED were measured on an Omni-λ300 Monochomotor/Spectrograph. All the absorption and PL spectra were recorded at room temperature, or between approximately 20 and 23° C. A JEOL FasTEM-2010 transmission electron microscope (TEM) was used for observing the particle size and shape. The TEM specimens were prepared in a glove box, where purified PbSe QDs were dispersed in chloroform and dropped on carbon-coated copper grids, and then the solvent was evaporated off.

Figure 2:
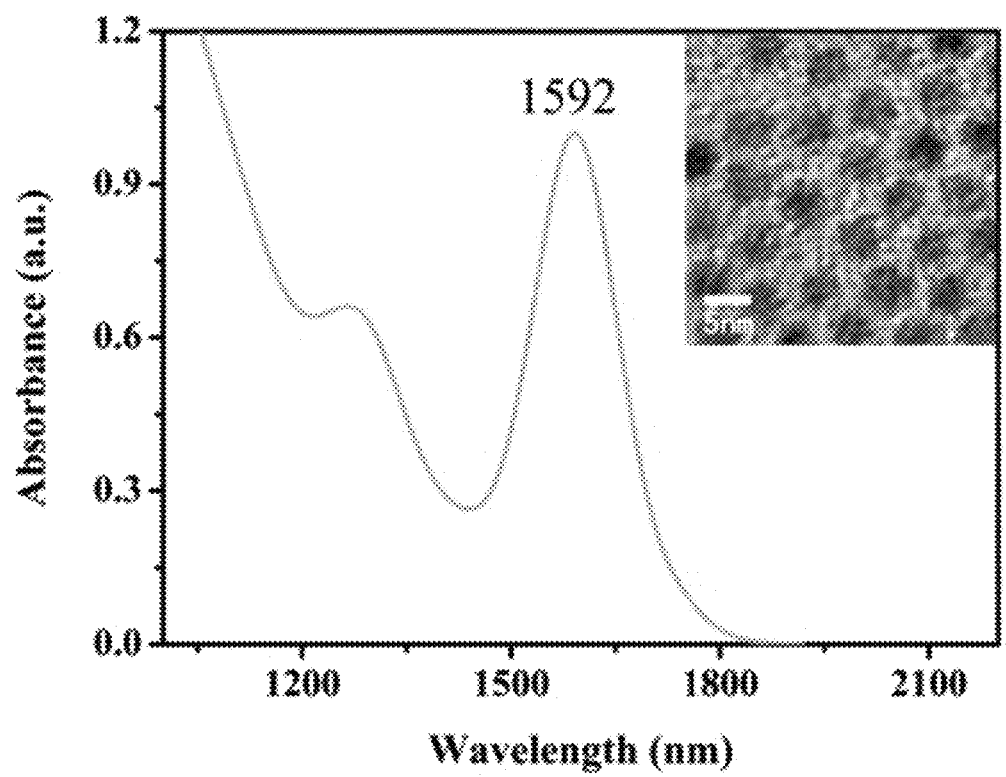
FIG. 2 is a normalized absorption spectrum and TEM image of 5.1 nm PbSe QDs.
Figure 3:
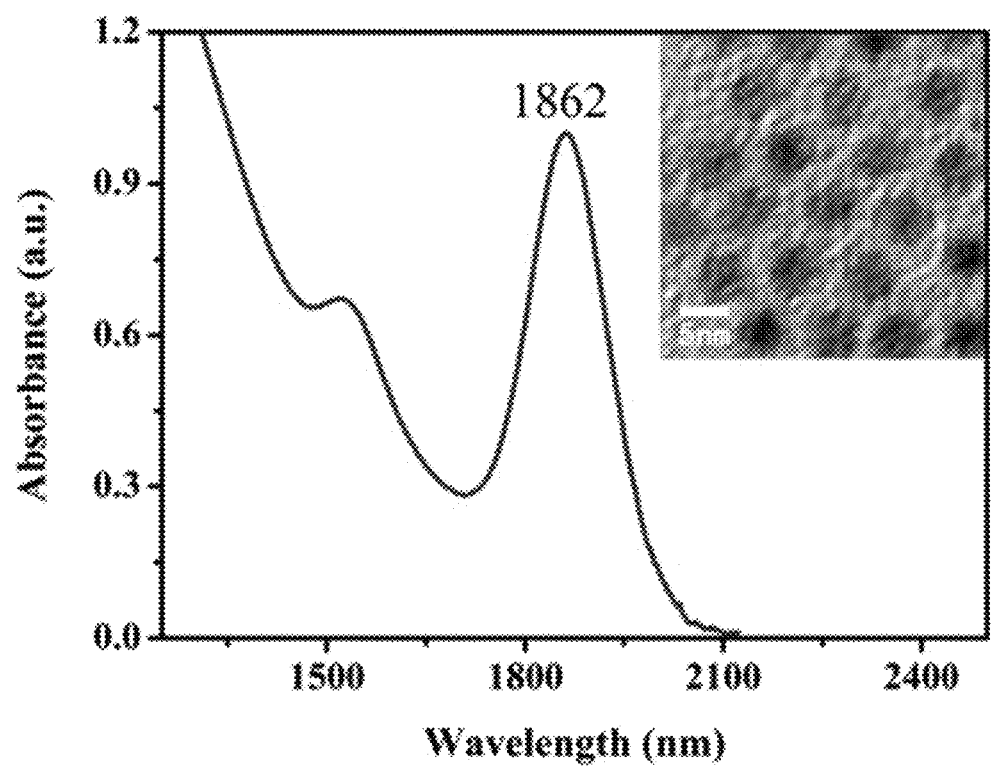
FIG. 3 is a normalized absorption spectrum and TEM image of 6.1 nm PbSe QDs.
Figure 4:
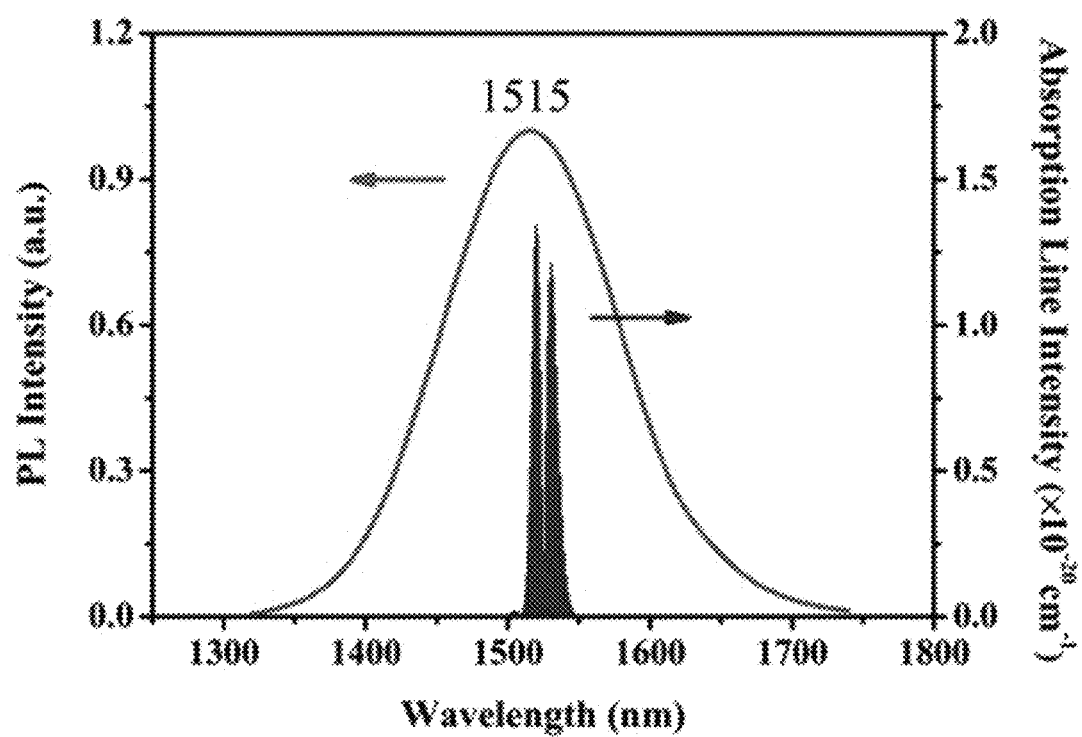
FIG. 4 is a normalized PL spectrum of 4.6 nm PbSe QDs and the covered absorption line intensities of $C_2H_2$ gas.
Figure 5:
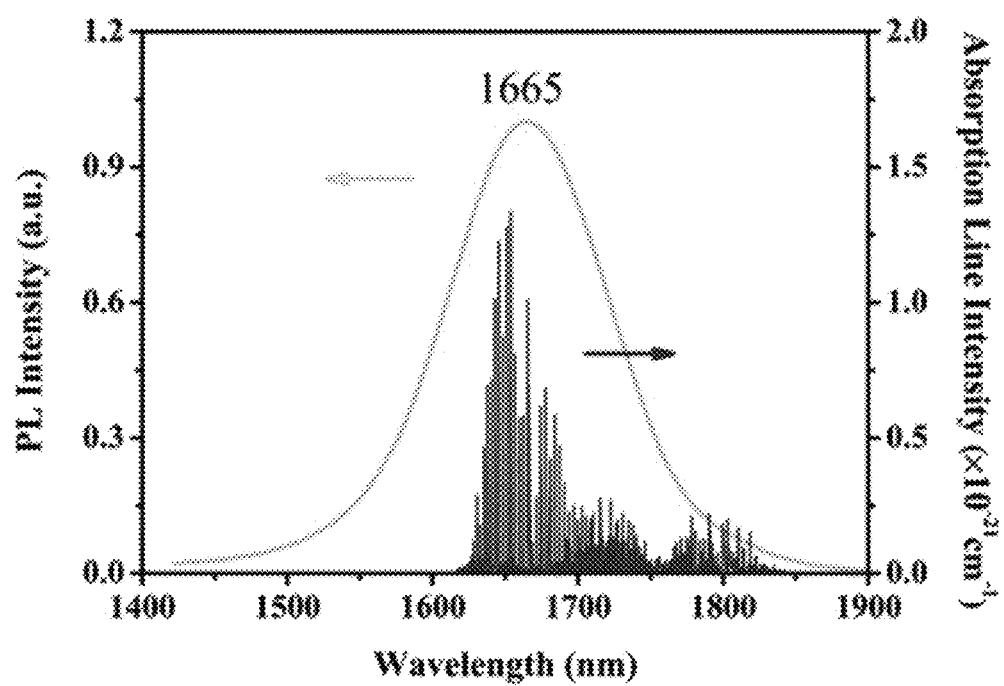
FIG. 5 is a normalized PL spectrum of 5.1 nm PbSe QDs and the covered absorption line intensities of $CH_4$ gas.
Figure 6:
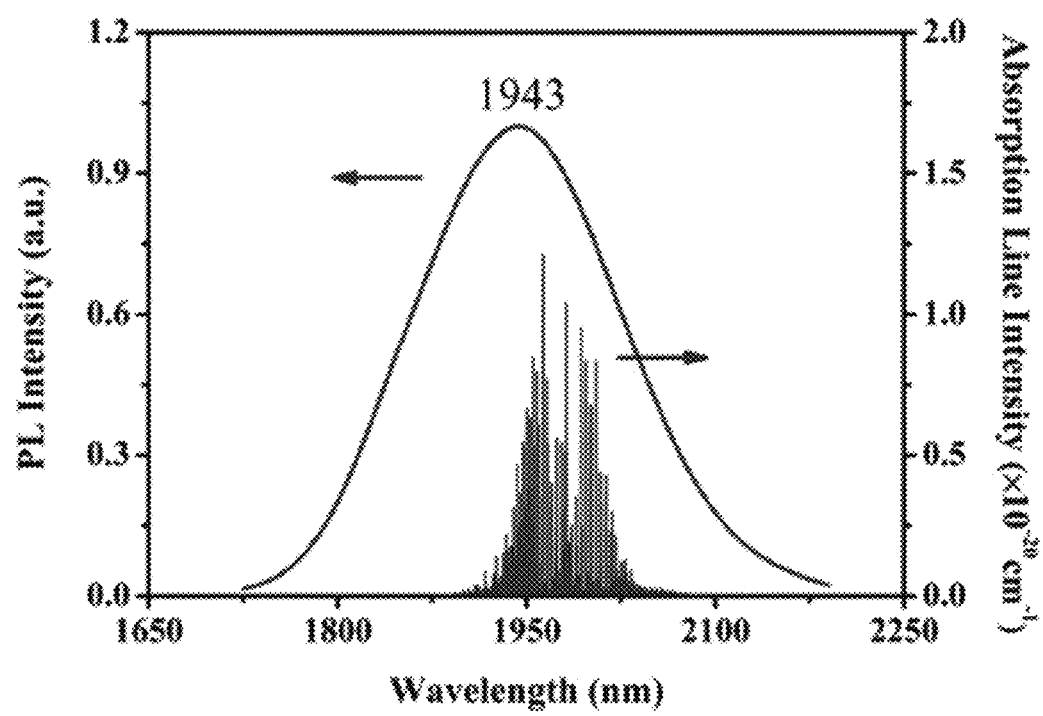
FIG. 6 is a normalized PL spectrum of 6.1 nm PbSe QDs and the covered absorption line intensities of $NH_3$ gas.

Three sets of PbSe QDs with respective particle sizes of 4.6, 5.1, and 6.1 nm were chosen. Their respective first absorption peaks of 1437, 1592, and 1862 nm are shown in FIGS. 1-3. FIG. 4 shows the PI, spectrum of 4.6 nm PbSe QDs and the absorption spectrum of $C_2H_2$. The PL peak of 4.6 nm PbSe QDs is 1515 nm with a full width at half maximum (FWHM) of 150 nm which covers the entire absorption spectrum of $C_2H_2$ gas (from 1500 to 1550 nm). The PL spectrum of 5.1 nm PbSe QDs has a PL peak of 1665 nm and a FWHM of 143 nm which, as shown in FIG. 5, corresponds to the $CH_4$ absorption spectrum. FIG. 6 indicates the PL peak of 6.1 nm PbSe QDs locates on 1943 nm with a FWHM of 185 DM; the main absorption spectrum of $NH_3$ from 1900 nm to 2060 nm is completely covered by this emission light. The highest absorption coefficients of $CH_4$, $C_2H_2$ and $NH_3$ are $1.33\times10^{-21}$, $1.34\times10^{-20}$ and $1.22\times10^{-20}$ $cm^{-1}$.

Figure 7:
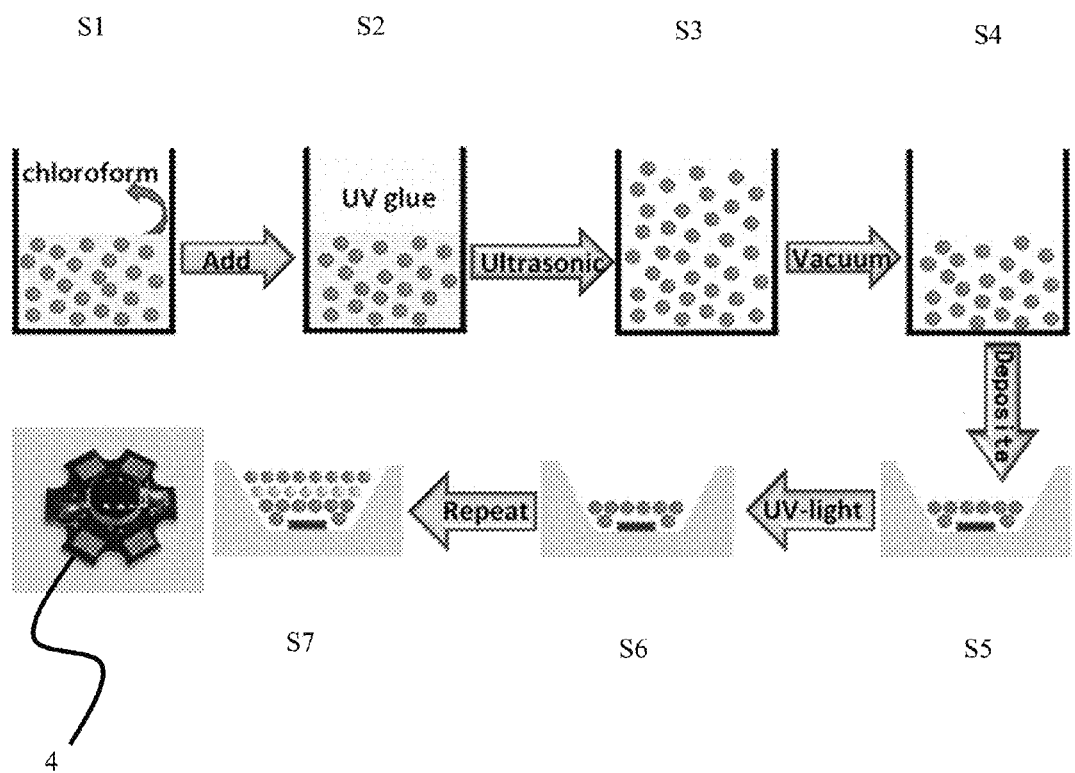
FIG. 7 is a schematic representation of the fabrication of near infrared (NIR) QD-LED with PbSe QDs.

An NIR LED based on PbSe QDs with three particle sizes was fabricated as shown in FIG. 7. A blue (or ultraviolet) GaN LED was employed as the excitation light source and PbSe QDs were used as photoluminescent materials. In step S1 PbSe QDs were mixed with chloroform. In step S2 the PbSe QD/chloroform mixture was mixed with a UV glue. In step S3 the PbSe QD/chloroform/UV glue mixture as mixed by vortex and ultrasonic treatment to form a homogeneous mixture. In step S4 the mixture was transferred into a vacuum chamber to remove chloroform and bubbles. In step S5 the PbSe QDs/UV glue composites were applied on the GaN chip to form a layer. In step S6, steps S1-S5 were repeated two times. The first repeat resulted in a second sized PbSe QDs-UV glue composite being applied on top of the first layer to form a second layer. The second repeat resulted in a third sized PbSe QDs-UV glue composite being applied on top of the second layer to form a third layer. Wherefore, three thin layers with three (3) sizes of PbSe QDs were formed.

Figure 8:
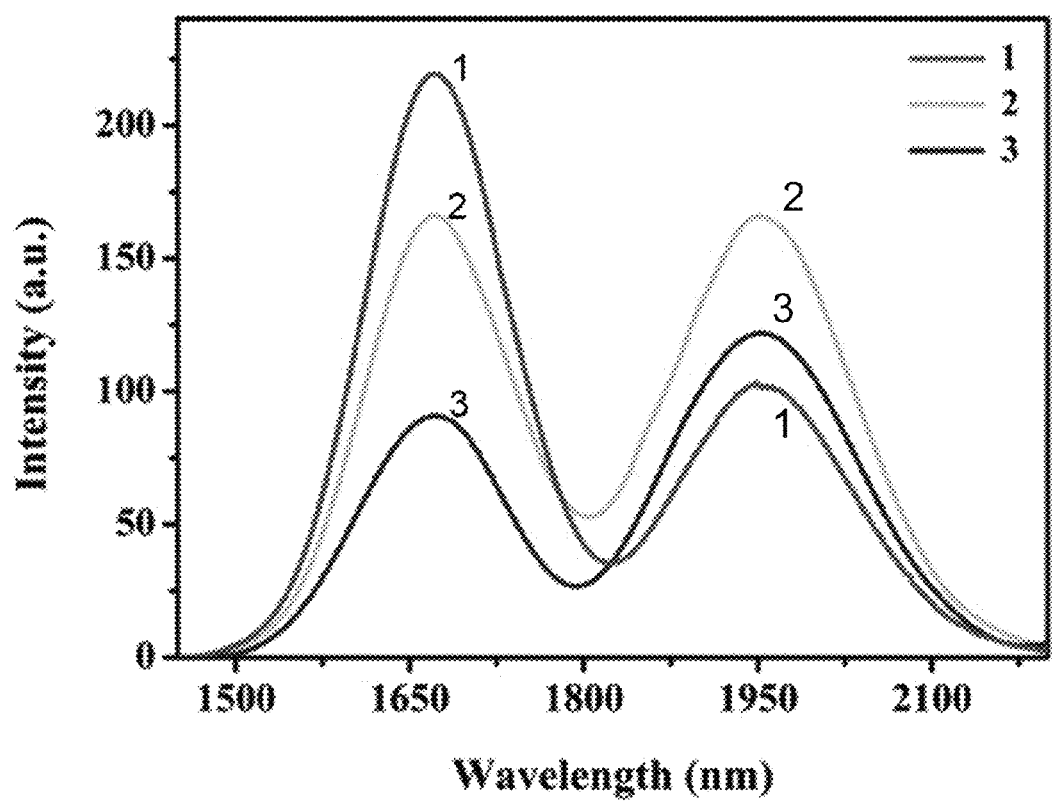
FIG. 8 is a variation of LED spectrum fabricated by different ways: (1) 5.1 nm PbSe CDs were deposited firstly followed by 6.1 nm PbSe QDs; (2) 6.1 nm PbSe QDs were deposited firstly followed by 5.1 nm PbSe. QDs; and (3) 5.1 and 6.1 nm PbSe QDs were mixed and deposited together.

According to FIGS. 1-6, the emission from QDs with small particle size will be absorbed by QDs with large particle size. If all the PbSe QDs with three particle sizes were mixed together, the device performance would be limited because of the reabsorption among different size QD nanoparticles, which will affect the output intensity of the LED device. FIG. 8 shows the different LED output intensity when using two sized QD nanoparticles with different layer formation as an example. Three LEDs were fabricated with 5.1 nm and 6.1 Tim PbSe QDs (the concentration of the two QDs in UV glue was $5\times10^{-3}$ $mmol \cdot L^{-1}$). 5.1 nm and 6.1 nm QDs-UV glue composites were deposited on the LED chip one after another which was named LED 1. Their thicknesses were adjusted to be 165.5 µm and 48 µm. Similarly, the deposition order changed and the thicknesses were kept the same then LED 2 was obtained. 5.1 nm and 6.1 nm QDs-UV glue composites were mixed at a 165.5:43 volume ratio, and then the mixture was deposited on the chip to form a film of 213.5 µm thick to get LED 3. After ultraviolet light curing, the LEDs' spectra were recorded as shown in FIG. 8. Compared with LED 2, the intensity of the emission spectrum of 5.1 nm QDs in LED 1 was stronger because much more blue light was absorbed by 5.1 nm QDs in LED 2. Due to the less blue light irradiating and the reflection of 5.1 nm QDs in LED 1, the intensity of emission spectrum of 6.1 nm QDs decreased seriously despite absorbing the light emitted by 5.1 nm QDs. Also, the emission spectrum intensities of 5.1 nm and 6.1 nm QDs in LED 3 decreased simultaneously compared with LED 2. After being mixed with 6.1 nm QDs, the light emitted by 5.1 nm QDs was absorbed significantly by 6.1 nm QDs. LED 2 demonstrated the well balanced emission which is the best.

This substantially no mutual-absorption layered structure proved to be an effective way to optimize the output intensity as it weakens the reabsorption between the QDs. Therefore, 6.1 nm PbSe QDs were firstly deposited on the GaN chip followed by 5.1 nm and 4.6 nm PbSe QDs to fabricate an NIR QD-LED with strong multiple emitting wavelengths. The concentration of PbSe QDs with different particle sizes in UV glue was at or about $5\times10^{-3}$ mmol·L$^{-1}$. QD's luminous intensity could be controlled by adjusting the PbSe QDs-UV glue composites thickness in this design. The thicknesses were determined to be 48.0, 165.5, and 671.5 μm for 6.1, 5.1, and 4.6 nm PbSe QDs, respectively.

Figure 9:
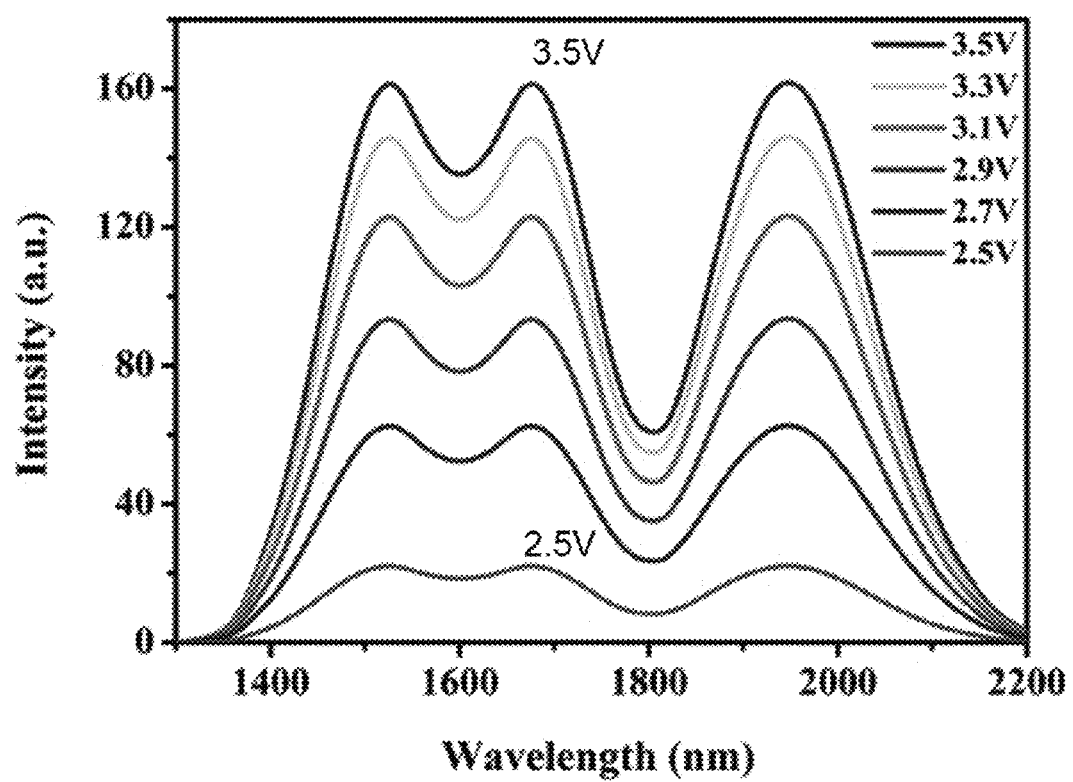
FIG. 9 is an evolution of a spectrum of a QD-LED, fabricated according to the method shown in FIG. 7, at different working bias from 2.5 to 3.5 V

The luminescence spectra of the as-fabricated NIR, QD-LED under different forward bias are shown in FIG. 9, in which the emission peaks of PbSe QDs were located at 1526, 1676, and 1949 nm, respectively. When the forward bias increased from 2.8 V to 3.2 V, the intensity of three emission peaks increased simultaneously with a good stability.

Figure 10:
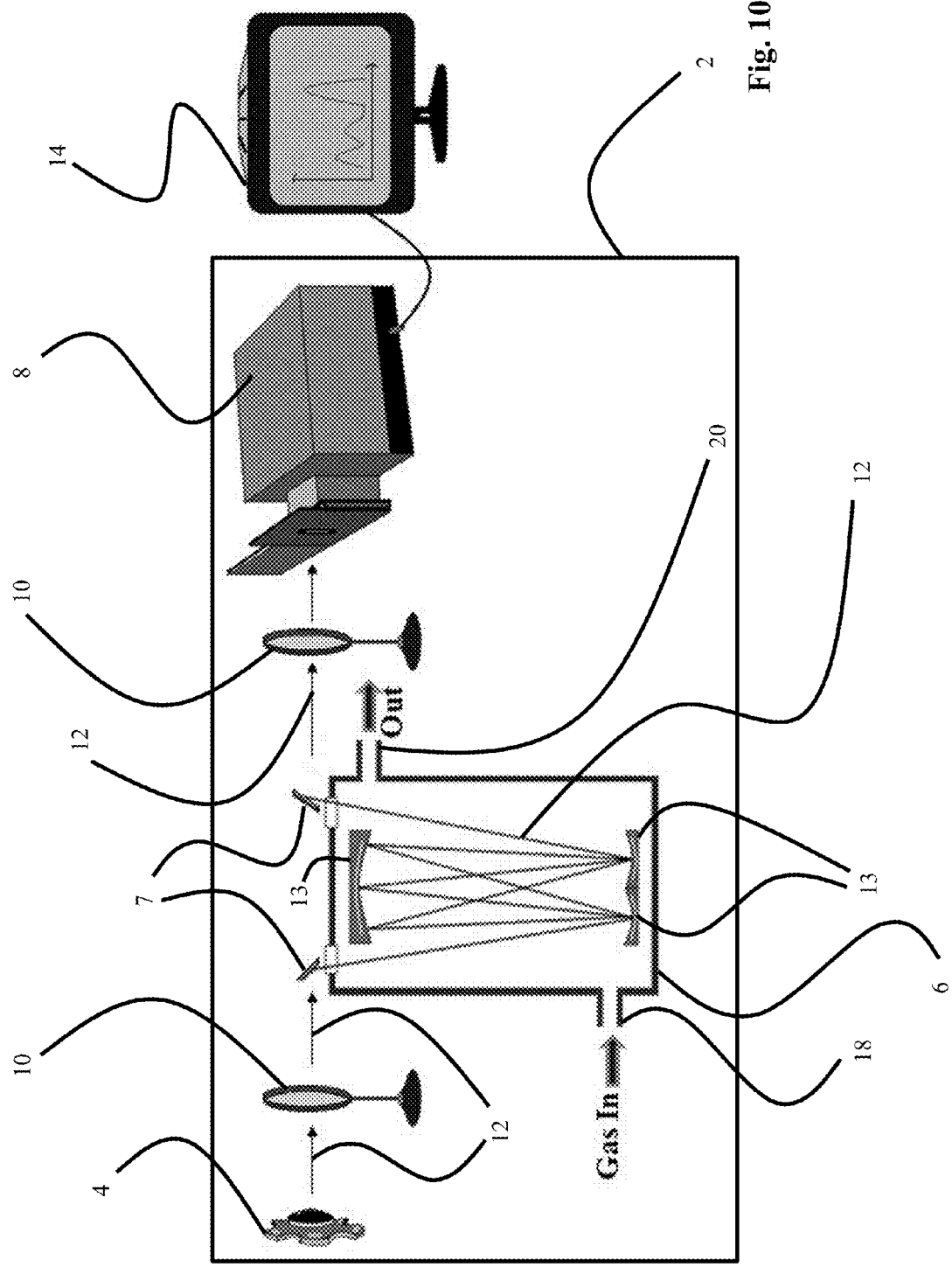
FIG. 10 is a schematic illustration of the detection setup.

EXEMPLARY QD-LED GAS DETECTION DEVICE. FIG. 10 shows an exemplary gas detecting device 2. This experimental setup consisting of the NIR QD-LED light source 4, the gas cell 6 and the optical spectrometer 8. Impulse voltage was employed to drive the light source 4. After being converged by the convex lens 10, an NIR beam 12 was transmitted through the gas cell 6. The light path "L" in this embodiment was 30 m. This light path is variable, and the gas cell size 6 can be very small with multiple reflection of the light 12. After passing through and out of the cell 6, the light beam 12 was directed to and was received by the optical spectrometer 8. The experimental data were collected and handled by a lock-in amplifier and a computer 14. Nitrogen and target gases 16 were loaded into the gas cell 6 in the same time but with different flow rates to obtain the different gas concentrations. According to Beer-Lambert law, when specific infrared radiation passes through the gas, the gas molecules absorb light energy:

$$I=I_0 e^{-KCL} \quad \text{(equation 1)}$$

where $I_0$ and I denote the input and output light intensities, respectively; K is the absorption coefficient of that gas; C is the gas concentration; and L is the cell length. It is worth noting that there is no filter needed in this system which is simpler, easier, and less expensive than current technology.

Figure 11:
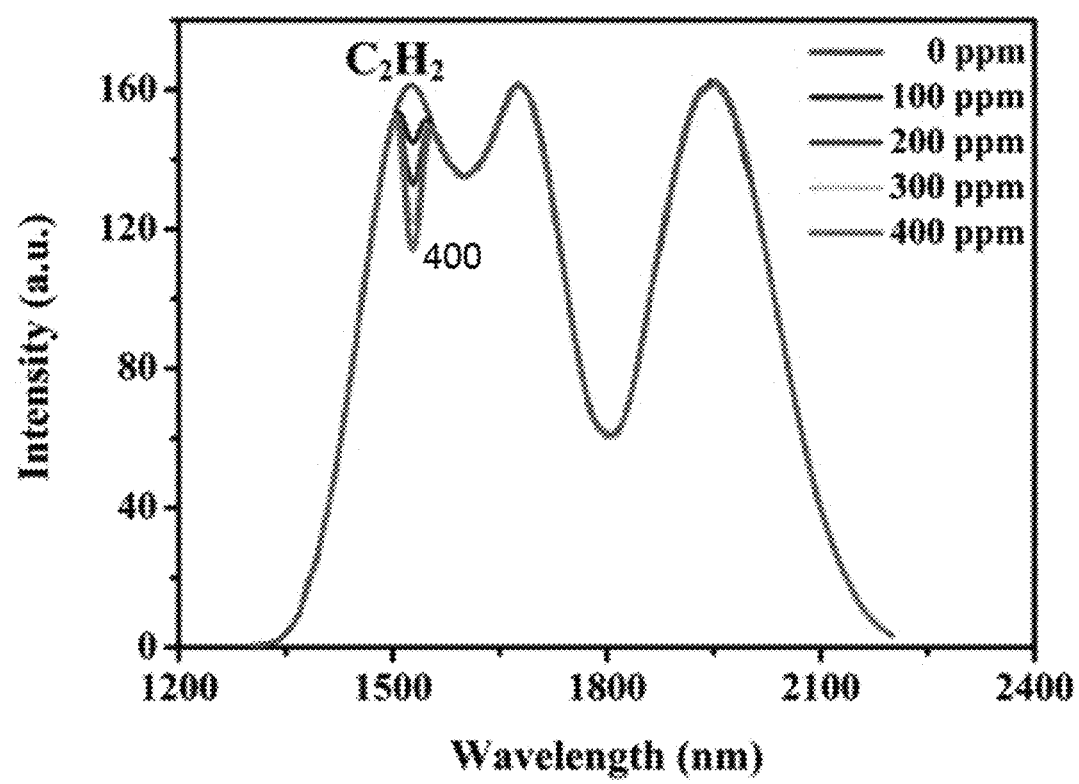
FIG. 11 is a PL spectrum of the LED after absorbed by a certain amount of single gas $C_2H_2$.

FIG. 11 shows the evolution of LED spectrum with the increasing concentration of $C_2H_2$ in $N_2$. Compared with the absorption line of $C_2H_2$ in FIG. 4, it is obvious that the intensity ranging from 1500 to 1560 nm decreased because of the absorption of $C_2H_2$ and the intensity at 1525 nm produces a maximal decline. The intensity lines on the graph at 1525 nm are, from the vertical highest to vertically lowest, 0, 100, 200, 300, and 400 ppm, the same order top to bottom as the values are listed in the key in the top right of the graph.

Figure 12:
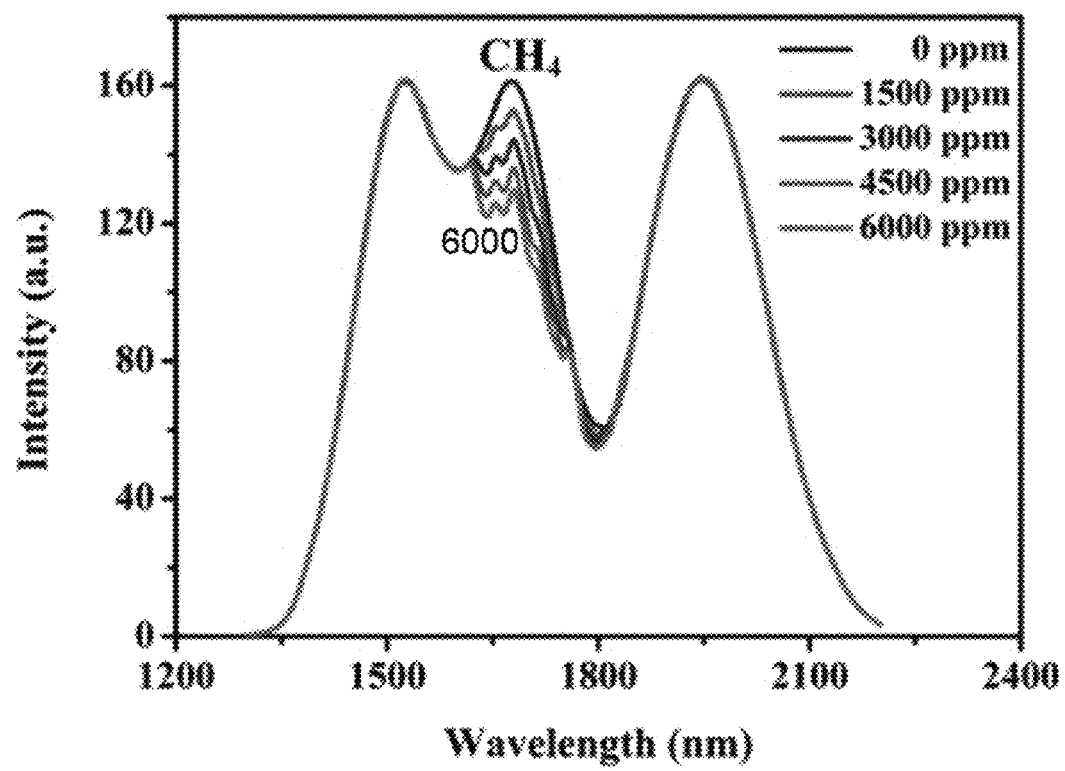
FIG. 12 is a PL spectrum of the LED after absorbed by a certain amount of single gas $CH_4$.

The variations of LED spectra with the increasing concentration of $CH_4$ in $N_2$ are shown in FIG. 12. The intensity lines on the graph at approximately 1700 nm are, from the vertical highest to vertically lowest, 0, 1500, 3000, 4500, and 6000 ppm, the same order top to bottom as the values are listed in the key in the top right of the graph. With the increase of concentration, the intensity of the PL peak decreases and this phenomenon conforms to Beer-Lambert law.

Figure 13:
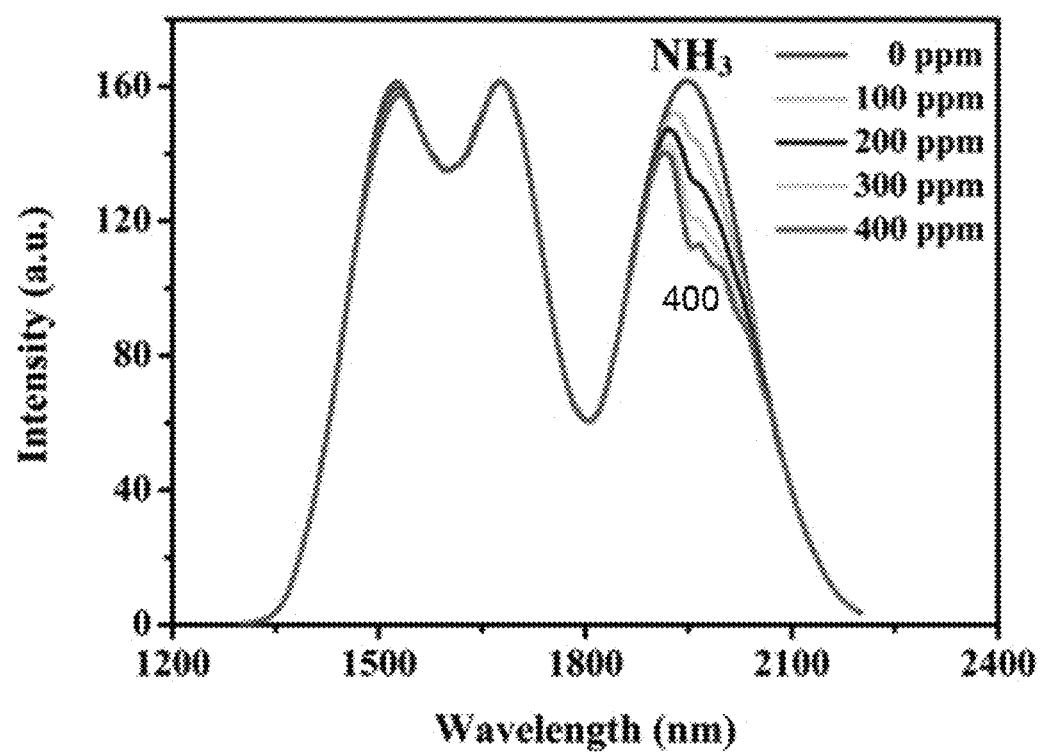
FIG. 13 is a PL spectrum of the LED after absorbed by a certain amount of single gas $NH_3$.

The same evolution was observed for $NH_3$ as shown in FIG. 13. The PL intensity at wavelengths of 1900 to 2060 nm dramatically decreases with the increase of $NH_3$ concentration. The intensity lines on the graph at 1950 nm are, from the vertical highest to vertically lowest, 0, 100, 200, 300, and 400 ppm, the same order top to bottom as the values are listed in the key in the top right of the graph.

Figure 14:
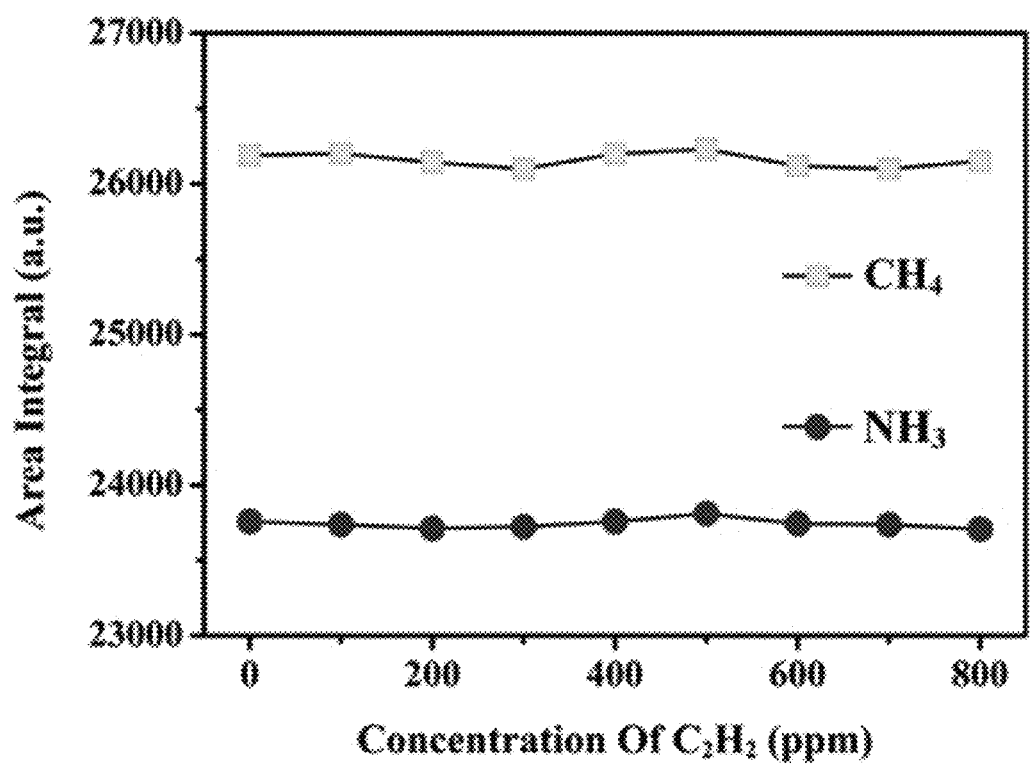
FIG. 14 is a variation tendency of optical power (area integral) of the other two PL peaks after absorbed by $C_2H_2$.
Figure 15:
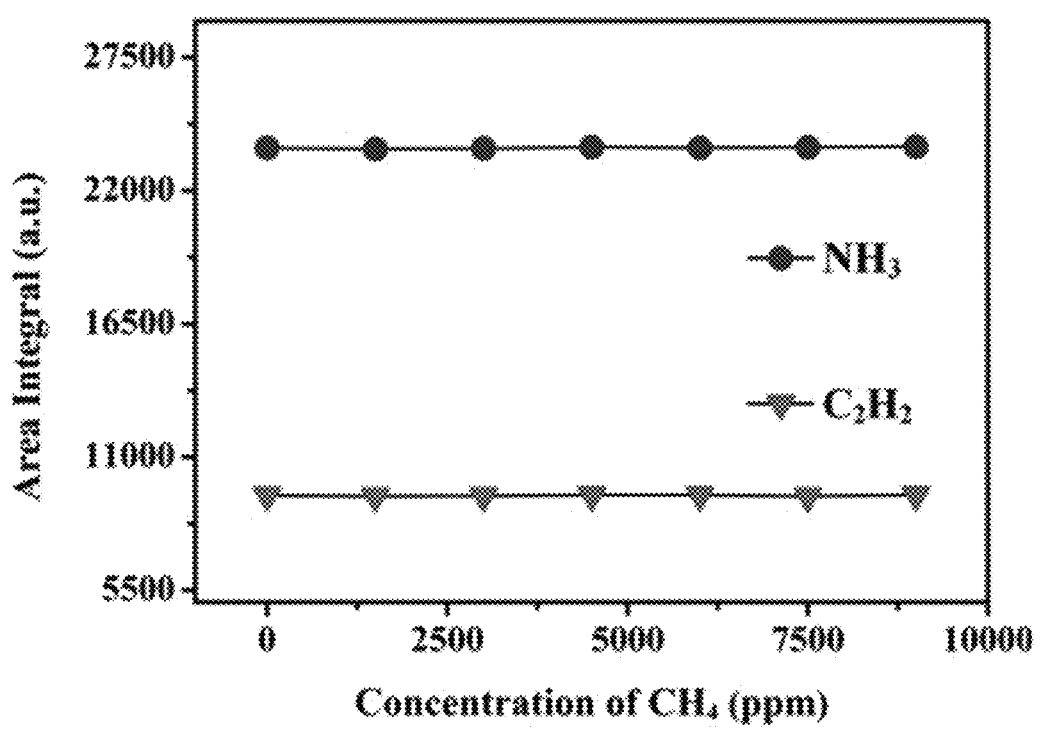
FIG. 15 is a variation tendency of optical power (area integral) of the other two PL peaks after absorbed by $CH_4$.
Figure 16:
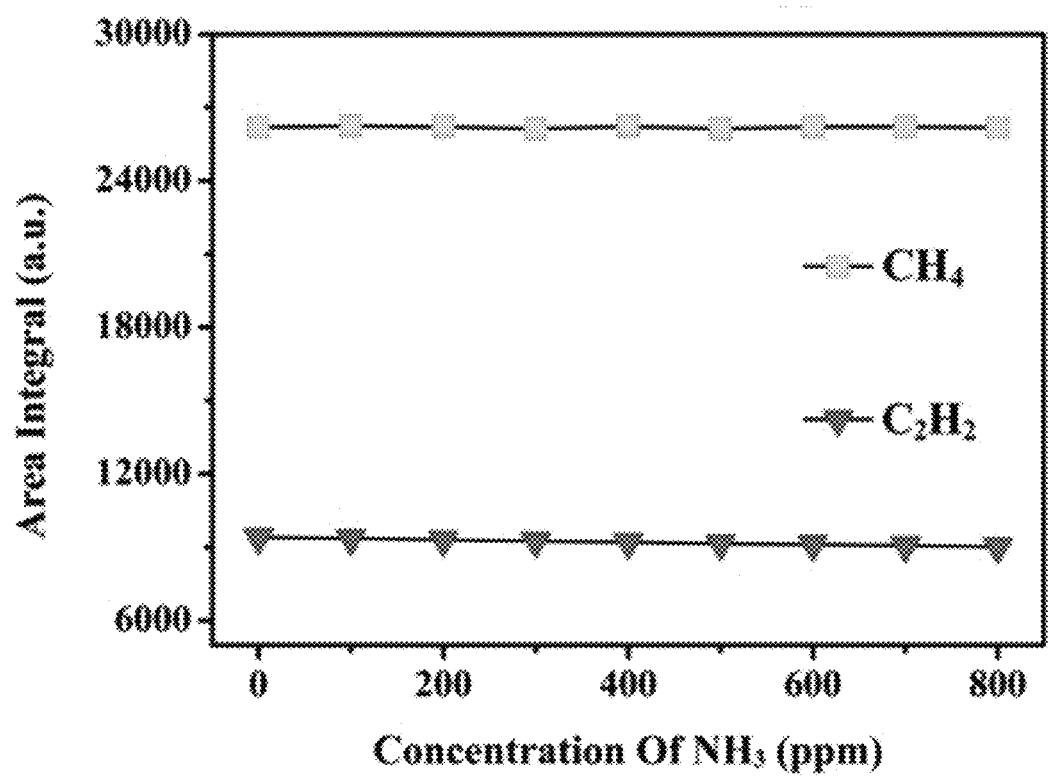
FIG. 16 is a variation tendency of optical power area integral) of the other two PL peaks after absorbed by $NH_3$.

When $C_2H_2$ with different concentrations was loaded into the gas cell, the area integral ranging from 1610 to 1840 nm and 1890 to 2070 nm corresponding to $CH_4$ and $NH_3$ absorption were analyzed according to FIG. 14. It is evident that the corresponding PL intensity was stable which meant the absorption of $C_2H_2$ barely affected the PL peaks relevant to $CH_4$ and $NH_3$. As shown in FIGS. 15 and 16, the same results were obtained when $CH_4$ or $NH_3$ was loaded into the gas cell. The conclusion was thus obtained that there was little interference in the measurement of one gas while the other two gases are present.

Figure 17:
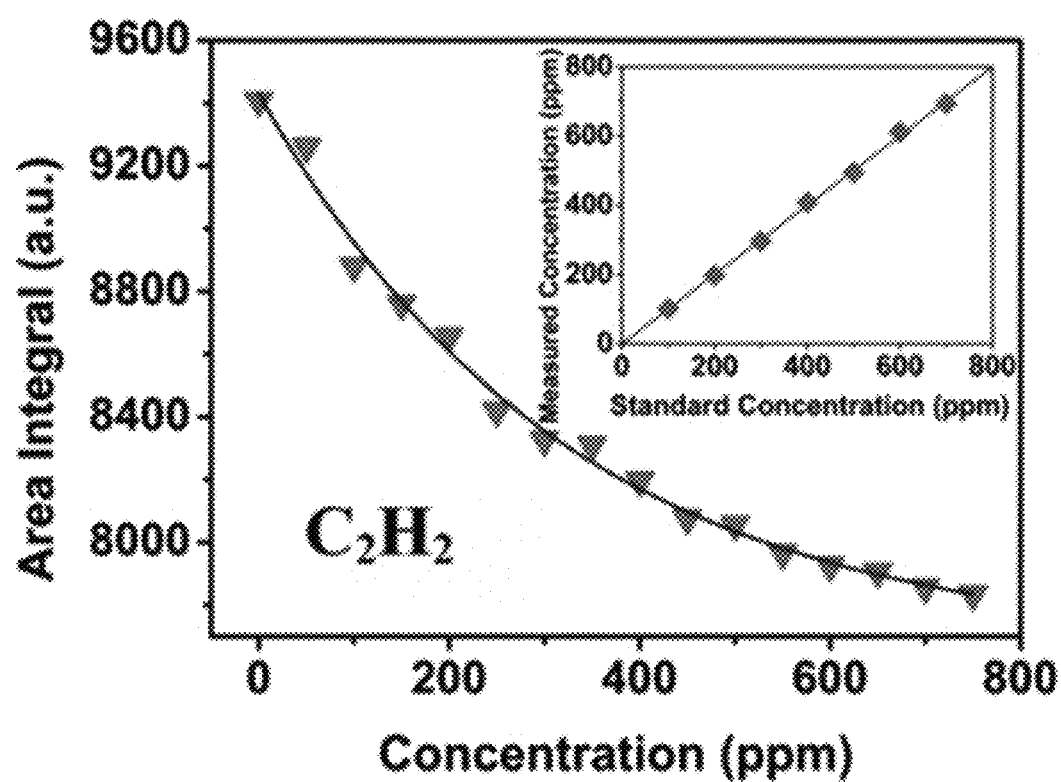
FIG. 17 is an area integral of PL spectrum of $C_2H_2$ at 15 standard concentrations and the working curve fitted by Matlab, with the inset showing the accuracy curve.
Figure 18:
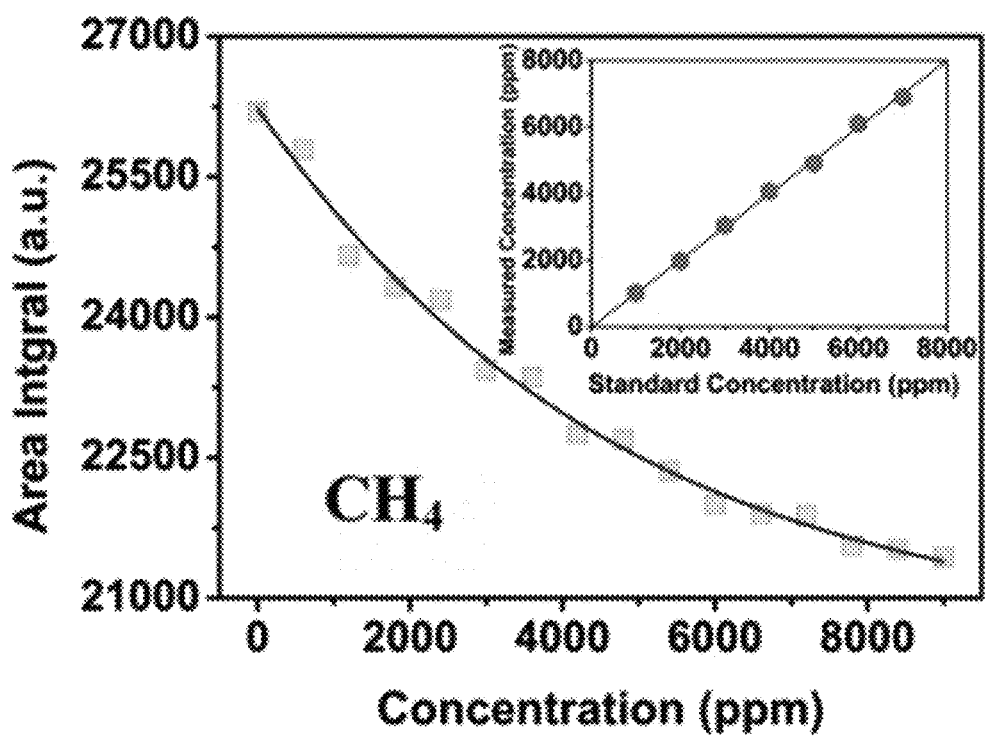
FIG. 18 is an area integral of PL spectrum of $CH_4$ at 15 standard concentrations and the working curve fitted by Matlab, with the inset showing the accuracy curve.
Figure 19:
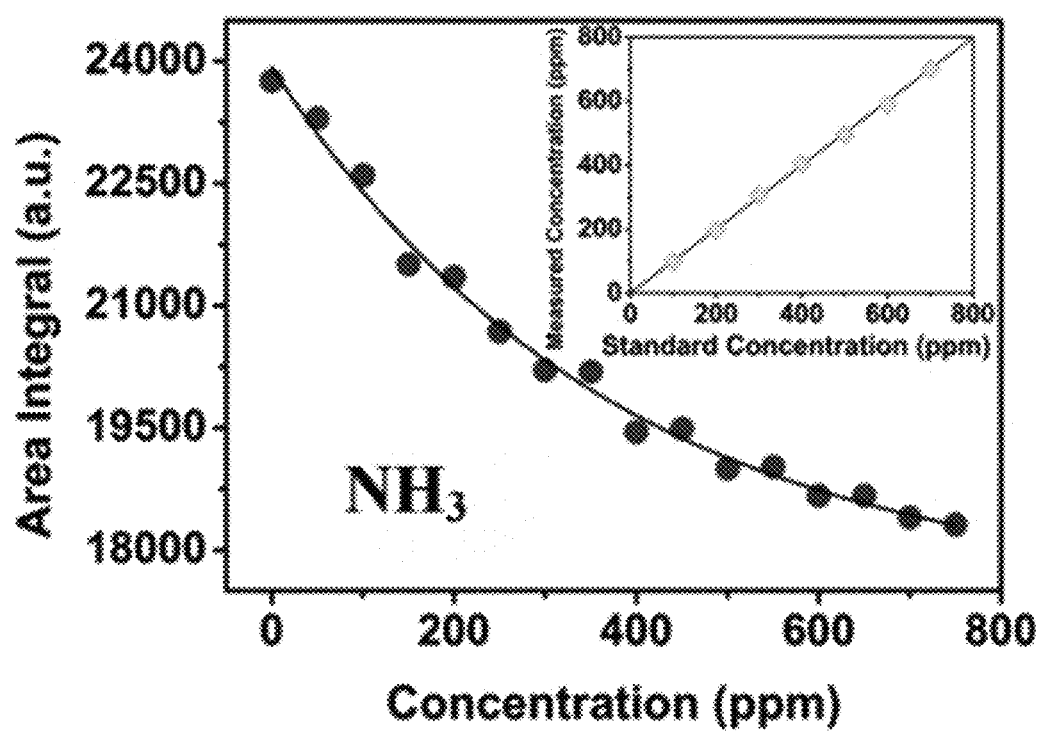
FIG. 19 is an area integral of PL spectrum of $NH_3$ at 15 standard concentrations and the working curve fitted by Matlab, with the inset showing the accuracy curve.

By using the designed system, the concentrations of a series of prepared $C_2H_2$ samples between 0-800 ppm were measured (20° C., 101.325 kPa). FIG. 17 shows the output signals at 15 standard concentrations of $C_2H_2$. The curve fitting was made using Matlab, and the fitting formula was obtained as:

$$y=1763\times e^{-x/318}+7667 \quad \text{(equation 2)}$$

where y is the area integral of the PL spectrum and x is the gas concentration. Different concentrations of $C_2H_2$, were analyzed and the calibrated formula was used to calculate the measured concentration to check the sensitivity and accuracy of the system. Comparing with the standard concentration, the accuracy curve is shown in FIG. 17 inset. The sensitivity was $2\times10^{-5}$ (20 ppm) and the accuracy was better than 2% [meaning the error rate was less than 2%]. The same calibrating experiment and accuracy analysis were performed to obtain the calibrated formulas of $CH_4$ and $NH_3$. FIGS. 18 and 19 show the integral output signals of PL spectra for $CH_4$ and $NH_3$. Their respective calibrated formulas were determined to be:

$$y=5670\times e^{-x/4683}+20563 \quad \text{(equation 3)}$$

and $$y=6474\times e^{-x/370}+17450 \quad \text{(equation 4)}.$$

The detection sensitivities of $CH_4$ and $NH_3$ were $1\times10^4$ (100 ppm) and $2\times10^{-5}$ (20 ppm), respectively. Because of a smaller gas absorption coefficient, the sensitivity of $CH_4$ was lower than those of $C_2H_2$ and $NH_3$. The same accuracy of 2% was obtained according to the insets of FIGS. 18 and 19.

Although a 3-gas simultaneous detection and measurement method and the device fabrication in NIR wavelength range are discussed and shown, based on the information disclosed, the device can be fabricated for simultaneous detection and measurement of four, five, six or more gases, including ten or more. Further, the number of gasses detected can also be enhanced by incorporating other sized PbSe, PbS, or PbTe QDs, as well as other NIR QDs and their core/shell variations. The disclosed process can also utilize ultraviolet (UV) emission QDs such as ZnS, ZnSe (and other UV QDs and their core/shell variations) and visible (VIS) emission QDs such as CdSe, CdTe (and other VIS Ws and their core/shell variations), as well as QDs of CdS, $CuInS_2$, InP (and other QDs and their core/shell variations that can emit light in more than one wavelength ranges, such as UV-VIS or VIS-NIR) for compact UV-VIS-NIR wavelength light sources for gas detection and measurement. This design can also be extended to IR range for QDs with good IR emission. In the Example, the two close PL peaks (in another word, wavelength) are 1515 nm and 1665 nm. Practically the peaks/wavelengths can be closer to work on more gases in the same time with any computer peak analysis programs. Some typical wavelengths of gasses that can be used for gas detection and measurement are: $SO_2$ (190-230 nm, 290-320 nm, 350-390 nm, 3.98 µm), CO (2.3 µm, 1.57 µm) $CO_2$ (2.7 µm, 4.33 µm), $H_2S$ (1576 nm).

Example

Figure 20:
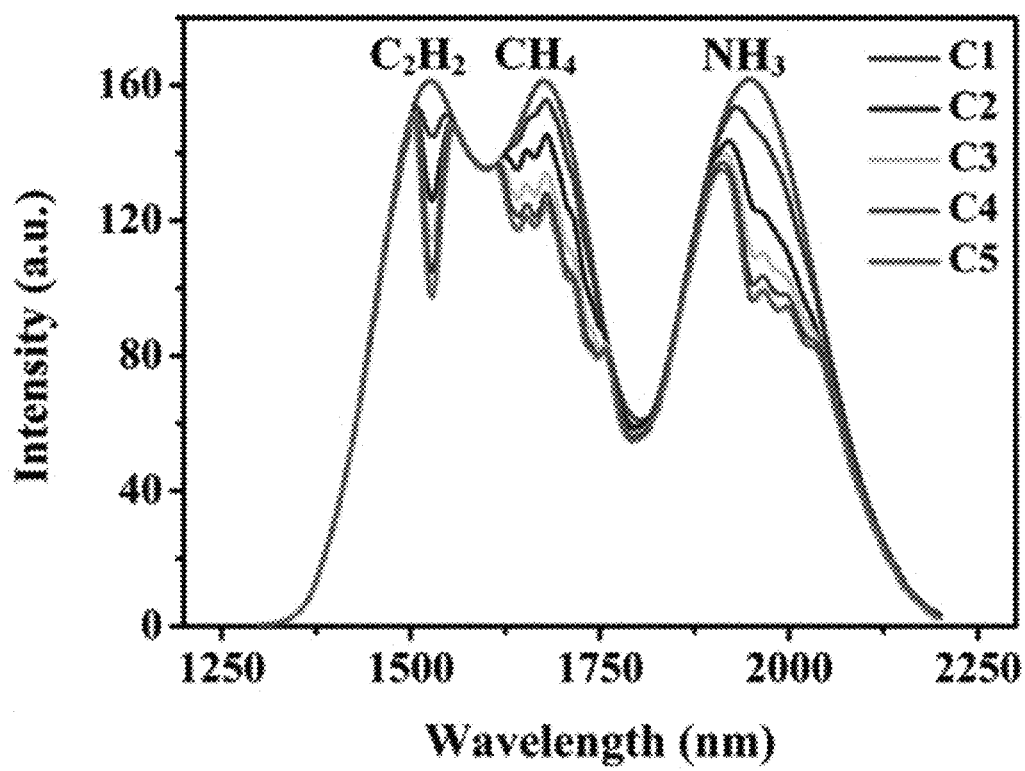
FIG. 20 is an evolution of LED spectrum with the concentration change of mixed gases.
Figure 21:
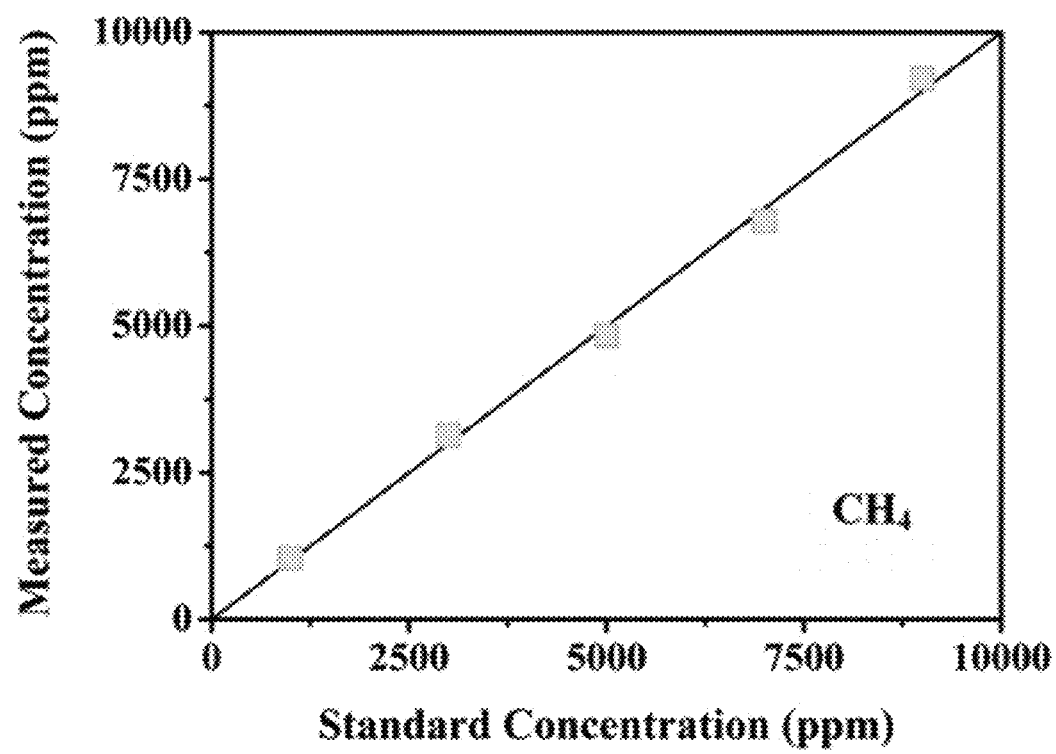
FIG. 21 is a comparison between standard and measured concentrations of $C_2H_2$ from FIG. 20.
Figure 22:
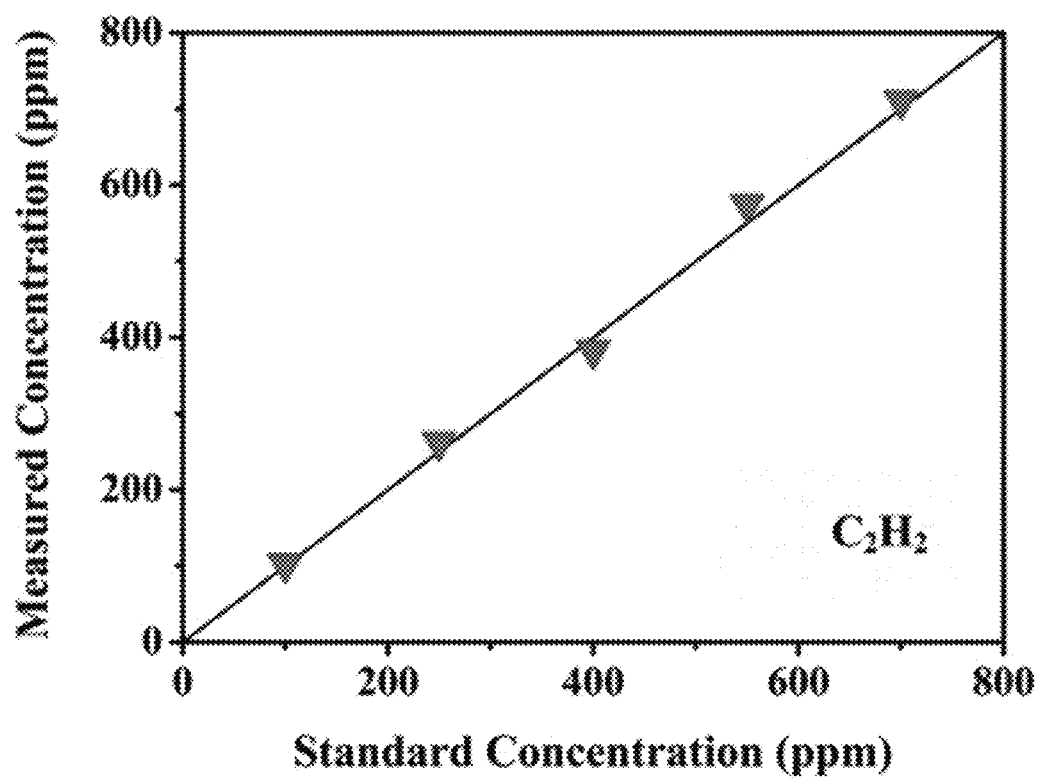
FIG. 22 is a comparison between standard and measured concentrations of $CH_4$ from FIG. 20.
Figure 23:
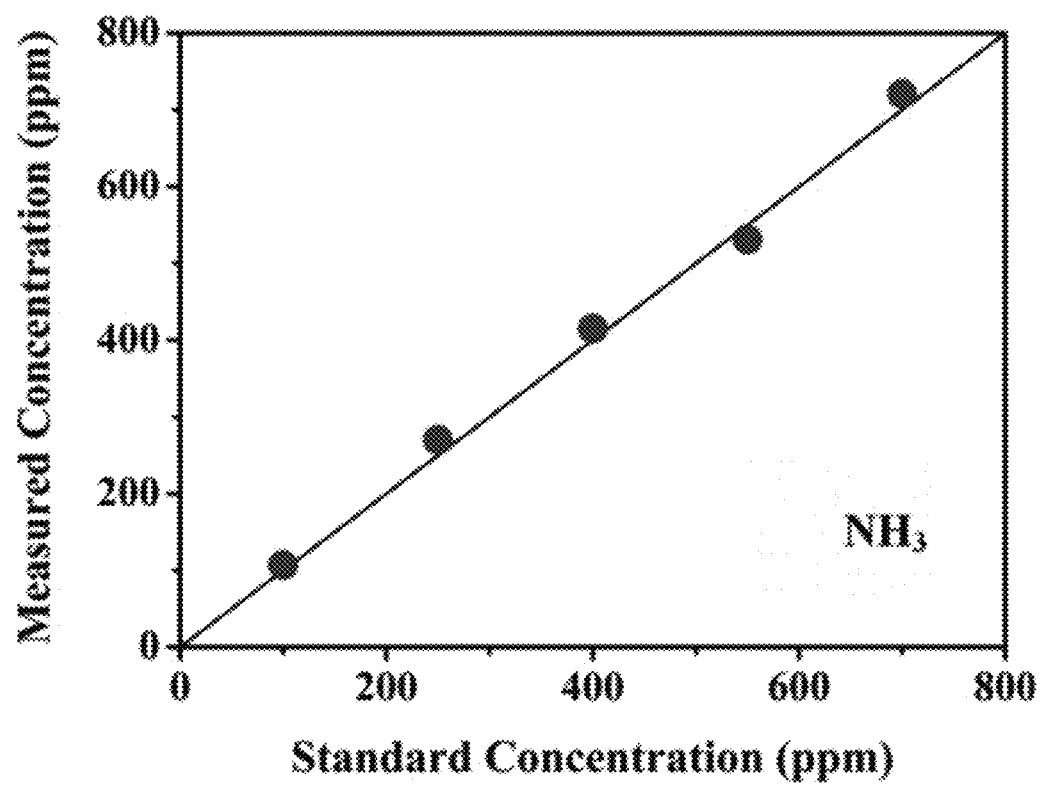
FIG. 23 is a comparison between standard and measured concentrations of $NH_3$ from FIG. 20.

Five (5) mixtures of $C_2H_2$, $CH_4$ and $NH_3$ with different ratios were loaded into the gas cell. FIG. 20 shows the corresponding PL spectra with the mixtures. The variation trend of the PL spectra of the mixed gasses was the same as the PL spectra with single gas. These examples also indicate that the interference among the three gases is little. Based on the above three fitting formulae, the method of cross calibration was adopted to determine the measured concentration. FIGS. 21-23 show the comparison between standard and measured concentrations for $C_2H_2$, $CH_4$ and $NH_3$, in mixtures, and their accuracies were all better than 2%. This as-fabricated NIR QD-LED can detect $C_2H_2$, $CH_4$ and $NH_3$ simultaneously and with the same high accuracy as when examined separately.

While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

I claim:

1. A gas detection device comprising:
    a light emitting source including a first plurality of quantum dots of substantially discrete size and made of one or more semiconductor materials;
    a gas cell to contain the gas to be detected;
    a light detector; and
    the light emitting source including at least three layers, the first layer having a first thickness and including the first plurality of quantum dots and not a second or a third pluralities of quantum dots, the second layer having a second thickness, which is more than twice as thick as the first thickness, and including the second plurality of quantum dots and not the first or the third pluralities of quantum dots, and the third layer having a third thickness, which is more than twice as thick as the second thickness, and including the third plurality of quantum dots and not the first or section pluralities of quantum dots.

2. The gas detection device of claim 1 wherein the cell includes a convex mirror arrangement to increase a light path through the gas cell to multiple times a length of the gas cell.

3. The gas detection device of claim 1 wherein the second plurality of quantum dots are of substantially discrete size, and the first plurality of quantum dots are one of substantially different size, substantially different composition, and both substantially different size and substantially different composition compared to second plurality of quantum dots.

4. The gas detection device of claim 3 wherein the third plurality of quantum dots are of substantially discrete size, and the third plurality of quantum dots are one of substantially different size, substantially different composition, and both substantially different size and substantially different composition compared to each of the first and the second plurality of quantum dots.

5. The gas detection device of claim 1 wherein the first plurality of quantum dots include at least one of Pb, Se, S, Te, Zn, Cd, Cu, In, P, and a combination thereof.

6. The gas detection device of claim 1 wherein the first plurality of quantum dots include at least one of PbSe, PbS, PbTe, ZnS, ZnSe, CdSe, CdTe, CdS, $CuInS_2$, and InP.

7. The gas detection device of claim 1 wherein the first plurality of quantum dots are between 4 nm and 7 nm in diameter in size.

8. The gas detection device of claim 1 wherein the first plurality of quantum dots exhibit photoluminescence with a wavelength emission in at least one of Infra-red, Near Infra-Red, visible, and ultraviolet wavelengths of light.

9. The gas detection device of claim 1 wherein the light emitting source includes a multi-wavelength light emitting diode.

10. The gas detection device of claim 9 wherein the multi-wavelength light emitting diode does not exhibit mutual-absorption.

11. The gas detection device of claim 1 wherein the first plurality of quantum dot includes a material with a quantum yield of at least 85%.

12. A method of detecting one or more gasses using a light emitting source having at least a first plurality of semiconductor quantum dots of substantially discrete size, a gas cell to contain the gas to be detected and a light detector, with the light emitting source including at least three layers, the first layer having a first thickness and including the first plurality of quantum dots and not a second or a third pluralities of quantum dots, the second layer having a second thickness, which is more than twice as thick as the first thickness, and including the second plurality of quantum dots and not the first or the third pluralities of quantum dots, and the third layer having a third thickness, which is more than twice as thick as the second thickness, and including the third plurality of quantum dots and not the first or section pluralities of quantum dots, the method comprising the steps of:
    energizing the light emitting source;
    emitting first light waves from the first plurality of quantum dots; and
    passing the first light waves through a gas sample in the gas cell and into a light detector.

13. The method of claim 12 wherein the second plurality of semiconductor quantum dots are of substantially discrete size and further comprising the step of emitting second light waves from the second plurality of quantum dots and passing the second light waves through the gas sample in the gas cell and into the light detector.

14. The method of claim 13 wherein the third plurality of semiconductor quantum dots are of substantially discrete size and further comprising the step of emitting third light waves from the third plurality of quantum dots, passing the third light waves through the gas sample in the gas cell and into the light detector, and the first, second, and third light waves are emitted at substantially a same first time and the first, second, and third light waves are detected at substantially a same second time.

15. The method of claim 14 wherein first layer is adjacent to one of a blue or ultraviolet light emitting diode chip; the first plurality of quantum dots has a first wavelength photoluminescence emission; the second layer is adjacent to the first layer and the second plurality of quantum dots has a second wavelength photoluminescence emission that is shorter than the first wavelength, and the third layer is adjacent to the second layer and spaced from the first layer by the second layer, and the third plurality of quantum dots has a third wavelength photoluminescence emission that is shorter than the first and the second wavelength.

16. The method of claim 13 further comprising the step of detecting two or more gases.

17. The method of claim 12 wherein the gas sample contains one of a single gas, more than one gas, and at least three gasses.

18. The method of claim 12 further comprising the step of detecting at least one gas.

19. The method of claim 12 further comprising the step of reflecting the first light waves off of mirrors and passing the first light waves through the gas sample more than once before passing the first light waves into a light detector.

20. A gas detection device comprising:
a light emitting source including a non-mutually absorption multi-wavelength light emitting diode;
the light emitting source including a first plurality of quantum dots of substantially discrete size, and made of a semiconductor material, a second plurality of quantum dots of substantially discrete size, and made of a semiconductor material, and a third plurality of quantum dots of substantially discrete size, and made of a semiconductor material;
the first plurality of quantum dots are one of substantially different size, substantially different composition, and both substantially different size and substantially different composition compared to second and the third plurality of quantum dots;
the second plurality of quantum dots are one of substantially different size, substantially different composition, and both substantially different size and substantially different composition compared to third plurality of quantum dots;
the light emitting source including at least three layers, the first layer, having a first thickness and including the first plurality of quantum dots and not the second or third pluralities of quantum dots, the second layer having a second thickness, which is more than twice as thick as the first thickness, and including the second plurality of quantum dots and not the first or third pluralities of quantum dots, and the third layer having a third thickness, which is more than twice as thick as the second thickness, and including the third plurality of quantum dots and not the first or second pluralities of quantum dots;
a gas cell to contain the gas to be detected;
the cell including a convex mirror arrangement to increase a light path through the gas cell to multiple times a length of the gas cell;
a light detector;
one of the first, the second, and the third pluralities of quantum dots includes at least one of PbSe, PbS, PbTe, ZnS, ZnSe, CdSe, CdTe, CdS, $CuInS_2$, and InP;
the first, the second, and the third pluralities of quantum dots are between 4 nm and 7 nm in size; and
the first, the second, and the third pluralities of quantum dots each exhibit photoluminescence with a wavelength emission in at least one of Infra-red, Near Infra-Red, visible, and ultraviolet wavelengths of light;
an emission peak for the first plurality of quantum dots is less than both an emission peak for the second plurality of quantum dots and an emission peak for the third plurality of quantum dots; and
the emission peak for the second pluralities of quantum dots is less than the emission peak for the third pluralities of quantum dots.

* * * * *